(12) United States Patent
DiFoggio (10) Patent No.: US 7,520,158 B2
(45) Date of Patent: Apr. 21, 2009

(54) METHOD AND APPARATUS FOR RESERVOIR CHARACTERIZATION USING PHOTOACOUSTIC SPECTROSCOPY

(75) Inventor: Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 254 days.

(21) Appl. No.: 11/439,861

(22) Filed: May 24, 2006

(65) Prior Publication Data
US 2006/0266109 A1 Nov. 30, 2006

Related U.S. Application Data

(63) Continuation-in-part of application No. 11/135,802, filed on May 24, 2005.

(51) Int. Cl.
*G01N 33/00* (2006.01)
(52) U.S. Cl. .................................. 73/19.1; 73/152.23
(58) Field of Classification Search .................. None
See application file for complete search history.

(56) References Cited

U.S. PATENT DOCUMENTS

| | | | |
|---|---|---|---|
| 4,492,862 A * | 1/1985 | Grynberg et al. | 250/255 |
| 5,942,440 A * | 8/1999 | Dooley et al. | 436/146 |
| 5,998,647 A | 12/1999 | Seki et al. | |
| 6,160,255 A | 12/2000 | Sausa | |
| 6,236,455 B1 | 5/2001 | Autrey et al. | |
| 6,608,683 B1 | 8/2003 | Pilgrim et al. | |
| 6,618,148 B1 | 9/2003 | Pilgrim et al. | |
| 6,662,040 B1 * | 12/2003 | Henrichs et al. | 600/431 |
| 6,792,354 B1 | 9/2004 | O'Meara et al. | |
| 6,930,193 B2 | 8/2005 | Yaghi et al. | |
| 7,039,447 B2 * | 5/2006 | Berman et al. | 600/316 |
| 2001/0022657 A1 * | 9/2001 | Autrey et al. | 356/432 |
| 2003/0143119 A1 | 7/2003 | Schwartz et al. | |
| 2003/0209058 A1 | 11/2003 | Merril | |
| 2005/0007583 A1 * | 1/2005 | DiFoggio | 356/301 |
| 2005/0117155 A1 | 6/2005 | Kosterev | |
| 2005/0252286 A1 * | 11/2005 | Ibrahim et al. | 73/152.55 |

FOREIGN PATENT DOCUMENTS

WO    WO 03/034043    4/2003

OTHER PUBLICATIONS

"Photoacoustic Water Vapour . . . ", Apr. 25, 2005, University of Szeged, 5 pages.
"Photoacoustic Water Vapour . . . ", Apr. 25, 2005, Univeristy of Szegad, 1 page.
"Photoacoustic Hydrogen Sulfide . . . ", Apr. 25, 2005, University of Szegad, 1 page.

(Continued)

*Primary Examiner*—Robert R Raevis
(74) *Attorney, Agent, or Firm*—Madan Mossman & Sriram PC (57) ABSTRACT

A method and apparatus are provided that assess reservoir compartmentalization by determining whether there are compositional differences such as whether the isotopic ratios of carbon (13C/12C) or of oxygen (17O/18O) are the same or different in various parts of the reservoir. A quartz enhanced photoacoustic spectrometer is provided for analysis of reservoir samples taken in various parts of the reservoir for comparison of geochemical composition to estimate reservoir compartmentalization.

17 Claims, 4 Drawing Sheets

OTHER PUBLICATIONS

"Assessing Reservoir . . . ", Apr. 25, 2005, www.oiltracers.com, 7 pages.
"Reservoir Oil Fingerprinting . . . ", May 3, 2005, www.humble-inc.com/rof_app99-2.htm, 18 pages.
"Using Mud Gas Logging . . . ", http://gaschem.com/mud.html, 3 pages.
"Using Gas Geochemistry to . . . ", www.gaschem.com/assess.html, 4 pages.
"Recognizing Reservoir . . . ", http://www.pttc.org/solutions/13.htm, 6 pages.
"Laser Photoacoustic . . . ", Feb. 1999, Foster et al., pp. 96S-108S.
"Trace-Gas Detection in Ambient . . . ", Dec. 2000, Kosterev et al., pp. 6866-6872.
"Recent Advantages of Trace Gas . . . ", Oct. 19, 2001, Tittel et al.
"Cavity Ringdown Spectroscopic . . . ", Oct. 20, 2001, Kosterev et al., pp. 5522-5529.
"Quartz-Enhanced Photoacoustic . . . ", Dec. 1, 2002, Kosterev et al., pp. 1902-1904.
Humble Instruments and Services; Reservoir Oil Fingerprinting (ROF); Nov. 29, 2004; Copyright 1999-2003; pp. 1-18.
University of Szeged—Photoacoustic Research Group; "Photoacoustic Water Vapour Measurement System for Natural Gas Industry"; Apr. 25, 2005; pp. 1-5.
University of Szeged—Photoacoustic Research Group; "Photoacoustic Water Vapour Concentration Measuring System For The Natural Gas Industry"; Apr. 25, 2005; p. 1.
University of Szeged—Photoacoustic Research Group; "Photoacoustic Hydrogen Sulfide Concentration Measuring System"; Apr. 25, 2005; p. 1.
Oiltracers (oiltracers.com); "Assessing Reservoir Compartmentalization Using Oil Geochemistry";Apr. 25, 2005; Copyright 1999-2005; pp. 1-7.
Kosterev, A. A. et al.; Rice Quantum Institute, Rice University, Houston, Texas; "Quartz-enhanced photoacoustic spectroscopy"; Published: Optic Letters, vol. 27, No. 21, Nov. 1, 2002; pp. 1902-1904.
Petroleum Technology Transfer Council; "Recognizing Reservoir Compartmentaliztion Increases Production"; Based on Workshop by PTTC's Rocky Mountain Region and Rocky Mountain Association of Geologists; Nov. 13, 1998; pp. 1-6.
Tittel, Frank K. et al., Rice University, Houston, TX; "Recent Advances of Trace Gas Sensors based on Infrared Semiconductor Lasers: Opportunities and Challenges"; Presented Industrial Affiliates Meeting, Rice, Oct. 19, 2001.
Kosterev, Anatoliy A. et al.; "Cavity ringdown spectroscopic detection of nitric oxide with a continuous-wave quantum-cascade laser"; Published: Applied Optics, vol. 40, No. 30, Oct. 20, 2001; pp. 5522-5529.
Foster,Nacy S. et al.; Laser photoacoustic spectroscopy; A versatile absorption-spectroscopic technique.; Published Feb. 1999.
Kosterev, Anatoliy A. et al.; Trace-gas detection in ambient air with a thermoelectrically cooled, pulsed quantum-cascade distributed feedback laser; Published: Applied Optics, vol. 39, No. 36, Dec. 20, 2000; pp. 6866-6872.
Oiltracers (Gaschem.com); "Using Gas Geochemistry to Assess Gas Reservoir Compartmentalization"; May 3, 2005; Copyright 1999-2005; pp. 1-4.
Oiltracers (Gaschem.com); "Using Mud Gas Logging (MGL) and stable isotope measurements to identify pay zones, assess hydrocarbon type, and evaluate reservoir compartmentalization"; May 3, 2005; Copyright 1999-2005; pp. 1-3.

* cited by examiner

METHOD AND APPARATUS FOR RESERVOIR CHARACTERIZATION USING PHOTOACOUSTIC SPECTROSCOPY

CROSS-REFERENCE TO RELATED APPLICATIONS

The present application is a Continuation-in-Part of U.S. patent application Ser. No. 11/135,802 filed on May 24, 2005, which is incorporated herein by reference.

BACKGROUND OF THE INVENTION

1. Field of the Invention

The present invention relates to the field of formation fluid sampling and analysis and in particular to the field of reservoir characterization using photoacoustic spectroscopy.

2. Background Information

To obtain hydrocarbons such as oil and gas, boreholes are drilled into the earth by rotating a drill bit attached to the end of a drill string. Modern directional drilling systems generally employ a drill string having a bottom hole assembly (BHA) and a drill bit at an end thereof that is rotated by a drill motor (mud motor) and/or by rotating the drill string. A number of downhole devices placed in close proximity to the drill bit measure certain downhole operating parameters associated with the drill string. Such devices typically include sensors for measuring downhole temperature and pressure, azimuth and inclination measuring devices and a resistivity-measuring device to determine the presence of hydrocarbons and water. Additional downhole instruments, known as logging-while-drilling (LWD) tools or measurement-while-drilling (MWD) tools, are attached to the drill string to determine the formation geology formation fluid characteristics and conditions during the drilling operations. Wireline logging tools are typically used after the drilling of the wellbore to determine formation geology and formation fluid characteristics.

Commercial development of hydrocarbon fields requires significant amounts of capital. Before field development begins, operators desire to have as much data as possible regarding the nature of the hydrocarbon formation in order to evaluate the reservoir for commercial viability. Despite the advances in data acquisition during drilling using the MWD tools and the analysis done by wireline tools after drilling the well, it is often necessary to analyze formation fluid from different wells at different locations in the reservoir. These samples are compared to estimate reservoir compartmentalization of the reservoir.

The degree of reservoir compartmentalization is important because it aids oil producers to decide on how to develop a reservoir (well location, types of production facilities, etc.). Oil producers want to know whether different sections of a reservoir are separate compartments (across which fluids do not flow) or whether they are connected. Separate compartments are drained separately and may need different types of processing for their fluids. Thus, there is a need for methods and apparatus for determining whether or not a reservoir is compartmentalized.

SUMMARY OF THE INVENTION

The present invention, in one aspect, provides a method and apparatus for photoacoustic spectroscopy (PAS) for analysis of reservoir samples to estimate compartmentalization of a reservoir. In one aspect of the invention a method and apparatus are provided for quartz-enhanced photoacoustic spectroscopy (QEPAS) for analysis of formation samples to estimate compartmentalization of the reservoir. The method and apparatus of the present invention provide for analyzing a first sample from a first location in the reservoir using a photoacoustic spectrometer (PAS); analyzing a second sample from a second location in the reservoir using the PAS; and comparing the analysis of the first sample to the analysis of the second sample to estimate reservoir compartmentalization.

In another aspect of the invention the PAS further comprises a quartz-enhanced PAS (QEPAS). In another aspect of the invention the analyzing further comprises estimating isotopic ratios for the samples, wherein the isotopic ratios further comprise at least one of the set consisting of isotopic ratios for carbon (13C/12C) or for oxygen (17O/18O). The method and apparatus can distinguish the spectrum of one type of molecule from that of another type of molecule (for example, CO versus $CO_2$) and can also distinguish the spectra of different isotopes of the same molecule (for example, $^{12}CO_2$ versus $^{13}CO_2$). In another aspect of the invention the QEPAS/PAS analysis is performed downhole. In another aspect of the invention the QEPAS/PAS analysis is performed at the surface.

Examples of certain features of the invention have been summarized here rather broadly in order that the detailed description thereof that follows may be better understood and in order that the contributions they represent to the art may be appreciated. There are, of course, additional features of the invention that will be described hereinafter and which will form the subject of the claims appended hereto.

BRIEF DESCRIPTION OF THE DRAWINGS

For detailed understanding of the present invention, references should be made to the following detailed description of the embodiment, taken in conjunction with the accompanying drawings, in which like elements have been given like numerals, wherein.

DETAILED DESCRIPTION OF THE INVENTION

The present invention, in one aspect, provides a method and apparatus or system to estimate and assess reservoir compartmentalization by determining whether or not the fluid geochemistry is the same in different parts or locations of the reservoir. "Reservoir compartmentalization" or compartmentalization refers to the presence of fluid flow barriers between two fluid sampling points. Similarly, "reservoir continuity"

refers to the absence of fluid flow barriers between two sampling points within a single well (vertical continuity) and/or the absence of lateral continuity barriers between two sampling points in discrete wells (horizontal continuity). For example, the system and method can be used to assess whether the isotopic ratios of carbon (13C/12C) or of oxygen (17O/18O) are the same or different in two or more samples taken from different parts of the reservoir. In one aspect, the present invention utilizes a tunable laser, which may be a tunable diode laser, in combination with an acoustic resonator to analyze reservoir samples. In one aspect, the present invention uses a photoacoustic spectroscopy (PAS) technique. The PAS may use a tunable diode laser in conjunction with an acoustic sensor such as a piezoelectric microphone to detect the sound waves generated when gas and vapors are pulsed by the laser beam. PAS can be sensitive to high downhole temperatures which may adversely affect a light sensor such as a photodiode but which has less effect on a PAS piezoelectric microphone. Repeating pulses of a laser, whose wavelength of light corresponds to the absorption wavelength of a particular gas, are sent through a gas and/or vapor mixture that is extracted from the formation fluid. When the targeted gas is present in the mixture, the targeted gas heats up with every pulse and cools down between pulses thereby creating a sound wave at twice the laser pulsation frequency. The detector provides electrical signals that correspond to the sound waves generated by the pulsating gas and/vapors. A processor analyzes the signals to determine the characteristics of the gas. A broadband acoustic detector is typically used.

In another aspect, the present invention may use a "Quartz Enhanced Photoacoustic Spectroscopy (QEPAS)." In one aspect, for QEPAS the laser light is pulsed at half the frequency of a high-Q resonant microphone (such as, a quartz tuning fork). The system can distinguish very subtle differences, such as isotopic differences, between reservoir samples which may be indicative of reservoir compartmentalization.

For liquid samples, such as formation fluids, a membrane can be provided to separate gas and/or vapors from the liquid so as to perform isotopic ratio analysis on the separated gas and vapor. The compartmentalization may be assessed by using analysis of phytane/pristine ratios of liquid crude oil or by using any other distinguishing features, such as any unexpected subtle differences in the fluid spectra that are capable of being resolved using a tunable optical filter.

Gravity segregation can cause some expected spectral differences in fluids from different depths even when there is no compartmentalization. For example, it is expected that the top of a column of crude oil will be more gas rich than the bottom of the same column of crude oil. However, if the reverse is observed and the bottom of a hydrocarbon column contains a higher percentage of low molecular weight hydrocarbons like methane and ethane than does the top of the column, then the system of the invention may determine that a seal between the upper and lower sections of the column exits and that the reservoir is compartmentalized. The same method may be used if one section of a hydrocarbon column has a different isotopic ratio of 13C/12C methane than does another section. Similarly, in a water column, a different isotopic ratio of 18O/17O water indicates that the water column is compartmentalized. The system of the present invention may be utilized to obtain information at various absorption wavelengths. For a 2 mm path length of investigation, the dominant liquid hydrocarbon's (C6+) optical absorption peaks are near 1725 nm and 1740 nm. The absorption peaks of hydrocarbon gases such as methane, ethane, propane, butane, lie between 1677 nm and 1725 nm.

Unexpected variations (variations not expected from gravitational segregation) in relative amounts of methane, ethane, propane, and so on can indicate compartmentalization. Also, subtle differences in spectra associated with differences in the amounts of non-hydrocarbon gases can also be evidence of reservoir compartmentalization. For example, H2S gas has a cluster of absorption peaks near 1952 nm and another weaker cluster of peaks near 1578 nm. Similarly, CO2 gas has a cluster of absorption peaks near 2007 nm and another weaker cluster of absorption peaks near 1572 nm. If one section of a hydrocarbon column has substantially more H2S or CO2 gas than does another section of that hydrocarbon column, and these differences cannot be explained by gravitational segregation, then the system of the present invention may use this anomaly as evidence that a seal is separating these two sections and that the reservoir is compartmentalized.

The system of the present invention may plot a series of many ratios (typically 5 to 10 ratios) of different compounds that can be plotted in a "star" pattern (polar coordinates). These ratios may be the percentages of ethane to methane or of phytane to pristine, and so on. Ratios of percentages may be used instead of the percentages themselves, because ratios can make more reliable oil-type indicators. To each such compositional ratio, we assign a different angle in the polar coordinate plot. Then, the distance from the center of the plot to a point represents the value of such a ratio for that point. Lines can be drawn to connect the plotted points to create polygons. In such plots, each type of oil is represented by a unique polygon. The polygon of one type of oil will not overlay the polygon that corresponds to a different type of oil. Thus, the system may assess or determine that there is evidence that the reservoir is compartmentalized when fluids from different parts of the reservoir have different compositional-ratio polygons. The system of the present invention may use hierarchical cluster analysis to demonstrate differences among formation hydrocarbons.

In another aspect, the system of the present invention may apply oil geochemistry (oil fingerprinting) or geochemical analysis to reservoir continuity assessment in a diverse range of geological settings (including a wide range of field sizes, structural environments, reservoir lithologies, and oil types). Petroleum geochemistry can provide an effective tool for identifying vertical and lateral fluid flow barriers within oil and gas fields.

In another aspect, the system of the present invention may use oil geochemistry to interpret ambiguous geological and/or engineering information. The approach is based on the proposition that oils from discrete reservoirs almost always differ from one another in composition. The technique assesses whether or not two oils are in fluid communication by comparing the relative compositions of each oil. The present invention, however, uses the PAS or QEPAS to determine the geochemical composition or content of a sample. A processor is provided by the present invention to compare the geochemical analysis of samples to estimate reservoir compartmentalization.

To arrive at an assessment of reservoir compartmentalization, the sample analysis may be integrated with any other available and relevant geological and/or engineering information (such as fault distributions, fault throws, fault shale/sand gouge ratios, lateral changes in reservoir lithology, formation fluid pressure versus depth data, pressure decline curves, oil-water contact depths, etc.).

Figure 1:
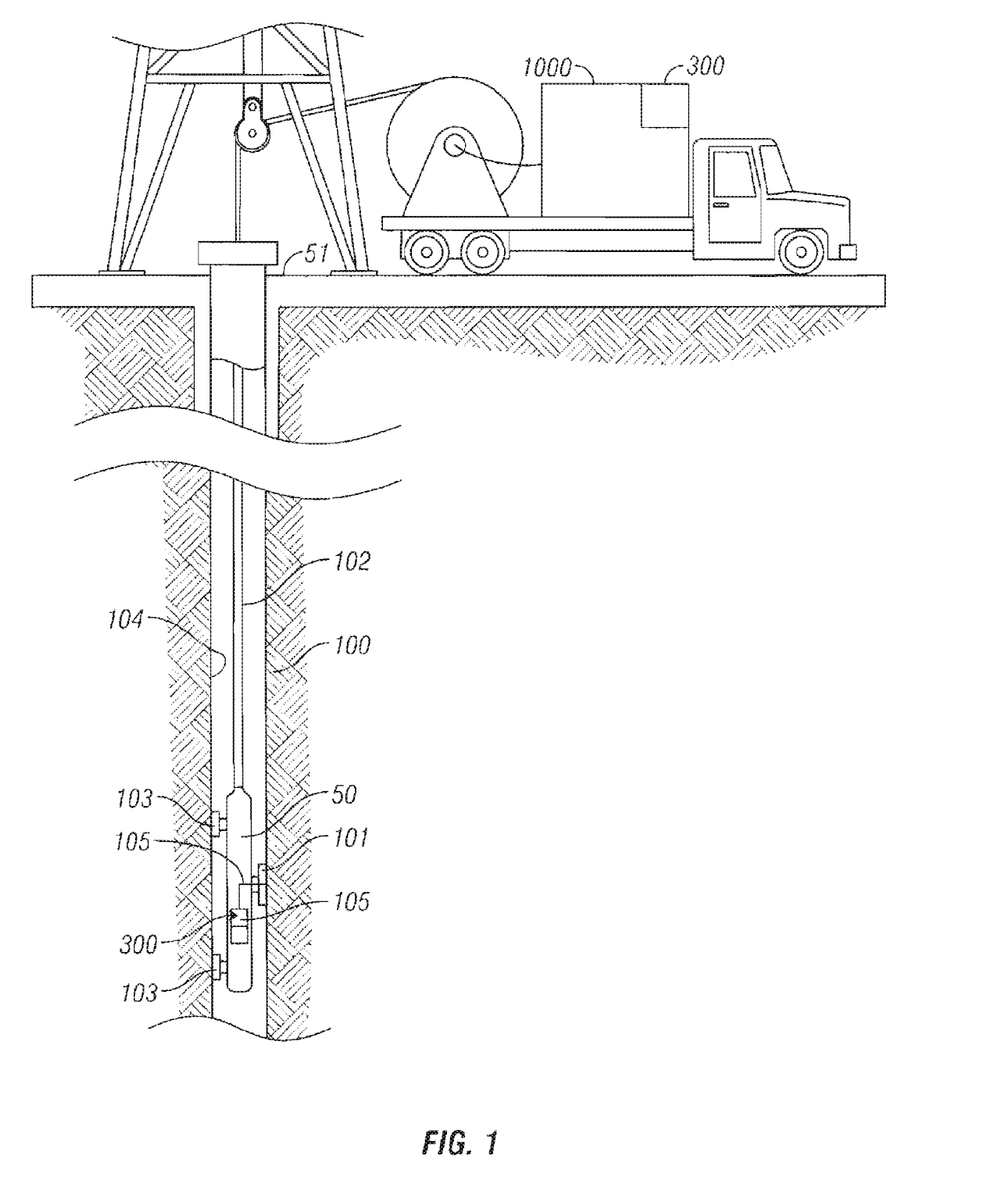
FIG. 1 is an illustration of a downhole tool deployed in a well from a wireline used to obtain and analyze formation fluids obtained from a formation within a reservoir.

FIG. 1 is an illustration of a downhole sampling tool 50 used in obtaining and analyzing reservoir samples, according to one embodiment of the invention. A gas analysis module 300, containing a QEPAS or PAS cell, laser cell, processor or computer, temperature control devices and other related equipment, is housed in the downhole tool 50. The module 300 may be utilized to analyze gas, vapors or liquids. The functions and operation of the analysis are described in more detail with reference to FIGS. 4-7. The module 300, in another aspects may also be placed at the surface 51 and controlled by the controller 1000. The module 300 may be self-sufficient downhole or parts of its operations and control may be performed by the surface controller 1000. In each case, the system described herein provides a method and apparatus for analysis of samples obtained from various parts of a reservoir and to estimate one or more parameters or characteristics relating to the formation fluid and estimation of reservoir compartmentalization. In the configuration of FIG. 1, the tool 50 is used to withdraw fluid samples at different locations in the reservoir and/or along a wellbore. Comparison of the analysis of two or more withdrawn fluids from different locations yields an estimate of the likelihood of reservoir compartmentalization.

Figure 2:
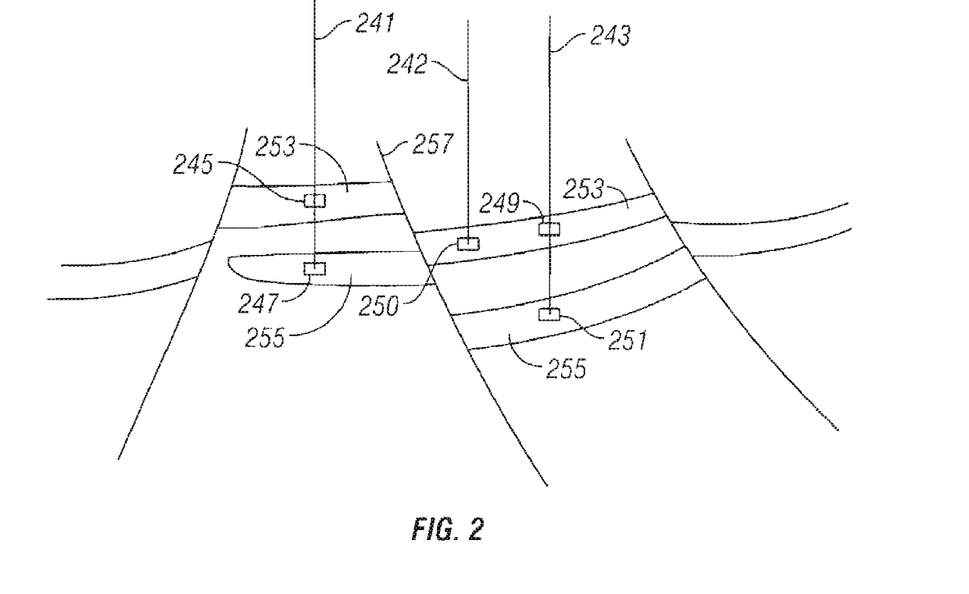
FIG. 2 is an illustration of a plurality of wells and samples taken to estimate reservoir compartmentalization.
Figure 3:
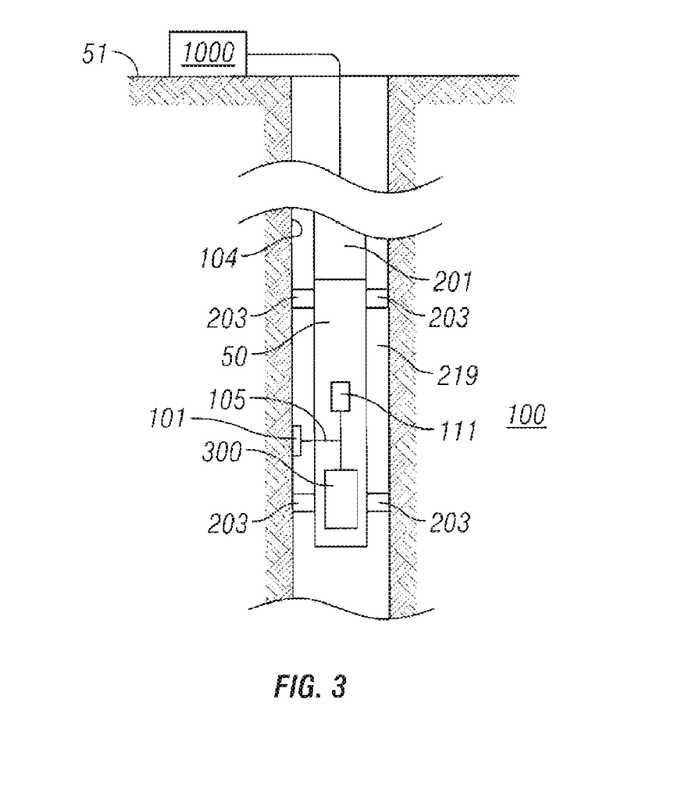
FIG. 3 is an illustration of a downhole tool deployed from a drill string used to obtain a sample from a formation within a reservoir.

FIG. 2 illustrates a simplified version of how the system of FIG. 1 and FIG. 3 may utilize the geochemistry composition and finger printing to assess reservoir continuity or conversely, compartmentalization. As an example only, FIG. 2 shows location of five sampling points 245, 247, 249, 250 and 251 in three wells 241, 242 and 243 that are located in zones 253 and 255. For illustration purposes, zones 253 and 255 are shown separated into two segments by a fault line 257. In the example of FIG. 2, the continuity of zone 253 between wells 242 and 243 will be suggested by the same geochemical composition or fingerprints from the samples 250 and 249. Compartmentalization (that is, no fluid communication) between zone 253 on the left side of fault line 257 and zone 253 on the right side of fault line 257 will be suggested by different geochemical composition or fingerprints between the samples 245 and 249 and 250. Similarly, the compartmentalization of zone 255 will be suggested from comparison of the geochemical compositions of samples 247 and 251. Additionally, comparison of sample 249 and 251 taken from the same well 243 can show different composition. The geochemical composition data can be integrated with additional geological and engineering data available for a reservoir. Additional geological engineering data may include, but is not limited to, pressure gradient, pressure decline curves, oil/water contact depths, gas oil ratios, permeability, viscosity, mobility, etc.

Returning now to FIG. 1, the tool 50 is shown deployed from a wire line 102 in a borehole 104 drilled in a formation 100. An extensible probe 101 placed against inside wall of the wellbore 104 extracts fluid from the formation 100. The extracted formation fluid flows through a flow line 105, where the gas analysis module 300 estimates or determines the composition or fingerprint of the formation fluid sample using a PAS or QEPAS. The fluid sample may be a gas, vapor or liquid. The system, in general, analyzes gas or vapors from the extracted fluid. Gas and/or vapors are separated from the liquid downhole for analysis, as described in reference to FIG. 4. Stabilizers 103 hold the tool 50 and extensible probe 101 in place during extraction of a formation fluid sample. The module 300 can perform the analysis downhole or alternatively may send the signals to the surface processor 1000 for processing and for providing the results.

FIG. 3 shows the deployment of the analysis module 300 in the well 104 by a drill string 201 for use during drilling of the wellbore. Straddle packers 203 or suitable anchoring devices hold the tool 50 in place during extraction of the fluid through the flow path 105 to the gas analysis chamber 300 containing the QEPAS/PAS of the present invention. The fluid may be extracted from the annulus 219 between the tool 50 and the well bore 104 or from the formation 100. The extracted fluid may be routed to a sample tank 111 or back to the well bore annulus 219. The results of the QEPAS/PAS analysis are acted on by the processor downhole or the sample can be sent to the surface 51 to be acted on by a surface analysis module and controller 1000.

Figure 4:
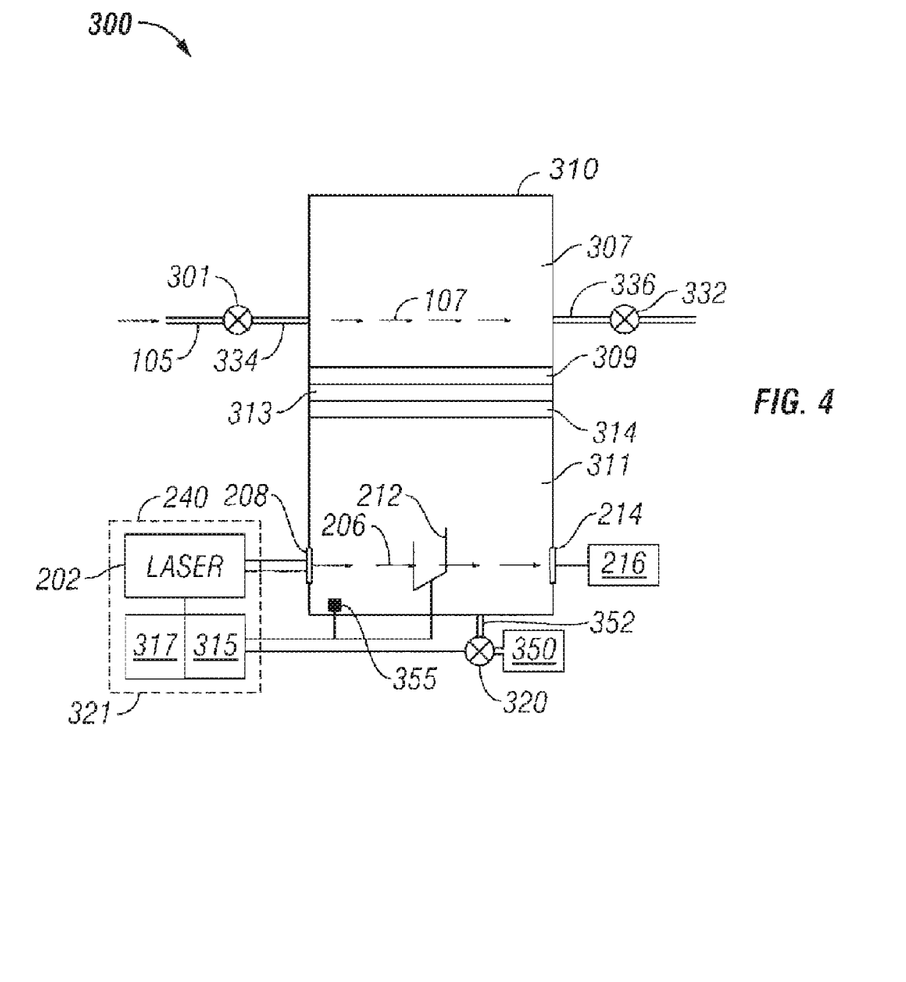
FIG. 4 is an illustration of a gas analysis module for performing Photoacoustic Spectroscopy (PAS) or Quartz Enhanced Photoacoustic Spectroscopy (QEPAS) according to one embodiment of the present invention.
Figure 5:
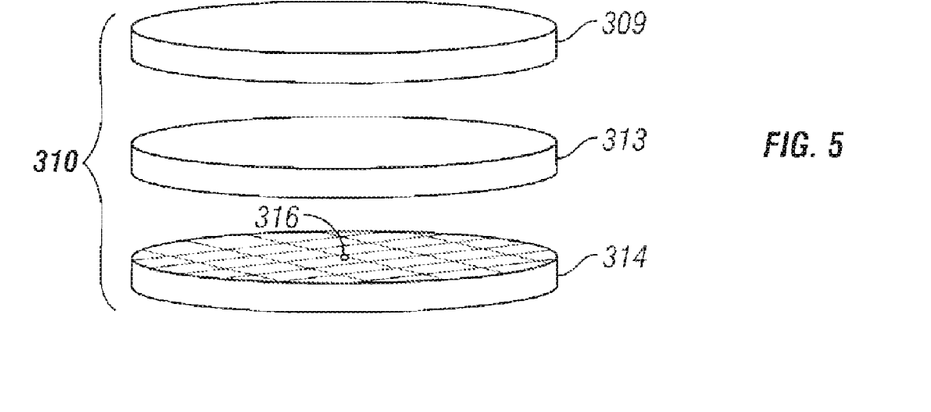
FIG. 5 is an illustration of an embodiment of semi-permeable membrane for use in the analysis module of FIG. 4 provided in an embodiment of the present invention.

Turning now to FIG. 4, a more detailed schematic of the gas analysis module 300 is shown according to one embodiment of the invention. The module 300 includes a fluid chamber or fluid sample cell 320 that has a fluid containment chamber 307 and a gas analysis chamber 311 that are separated by a semi-permeable membrane assembly 310 (FIG. 5). The module 300 also includes a laser 202, associated electronic circuitry 317 and a processor or computer 315. In one aspect, the module 300 may include a pump, such as an ion pump 320 to reduce the pressure in the gas analysis chamber 311, such as to atmospheric or sub-atmospheric pressure. In another aspect, the chamber 311 may be in fluid communication with a suitable sorbent to selectively remove formation fluid gases and vapors that have diffused into the chamber 311 as explained in more detail later. A sorption-cooling unit 240 may be provided to maintain the laser 202 and control electronics 315 within their operating and/or survival temperature range. As shown in FIG. 4, the formation fluid containment chamber 307 is separated from the low pressure gas analysis chamber 311 by the semi-permeable membrane assembly 310 that includes a semi-permeable membrane 309 a metal filter 313 and a metal plate that further includes one or more small holes 316. The metal plate provides mechanical strength between the relatively high pressure chamber 307 and the low pressure chamber 311, and the hole 316 provides a path for the gas and vapors to diffuse into the chamber 311. Thus, the formation fluid containment chamber 307 is positioned on one side of the semi-permeable membrane 309 and an (optionally evacuated) gas analysis chamber 311 on the other side of the semi-permeable membrane 309. The semi-permeable membrane 309 enables the gases and vapors trapped in the formation fluid sample in chamber 307 to diffuse across the semi-permeable membrane 309 into the gas analysis chamber 311 for analysis. For the purpose of this disclosure the term gas and vapor may be used interchangeably.

Formation fluid is extracted from the formation 100 and enters into the fluid containment chamber 307 via flow line 105 and valve 301. The formation fluid may be extracted via the probe 101 by a pump (not shown). The extracted fluid 107 flows into the chamber 307. A valve 332 coupled to the chamber 307 via a line 336 allows the formation fluid to flow across the chamber 307 and exit to another storage chamber or the wellbore 104. Dissolved gases and liquid vapors diffuse from the formation fluid on the fluid side of the semi-permeable membrane, through the semi-permeable membrane and into the chamber 311. To analyze the gas or vapor diffused in chamber 311, a laser 202 sends pulsed energy (beam) 2062 into the gas in chamber 311 via a window 208. The pulsed energy beam produces photoacoustic waves, whenever a gas is present that absorbs that laser's wavelength of light. An acoustic microresonator 212, which may include a tuning fork, placed in the chamber 311 detects the photoacoustic waves. The excitation of the tuning fork by the photoacoustic waves generates current that is converted into a voltage by the circuitry 317 and processed by the computer 315. The signals for the micro-resonator may be analyzed downhole and/or sent to the surface process or 1000 (FIGS. 1 and 3) for processing. The controller 315 controls the operation of the laser 202. The laser beam 206 in one aspect may pass through a second window 214. A portion of the laser beam passing through window 214 may be directed to a photodetector 216, the output of which may then be used to align the laser 202 to pass between the tines of the tuning fork. Alternatively, as described below, the laser beam from the laser 202 may be split and directed to reference cell, such as that utilizes a Fiber Bragg Grating (FBG) as described in reference to FIG. 6. An FBG that is made out of low thermal coefficient of expansion glass can be used as a wavelength standard for tuning the wavelength of the laser.

The fluid containment chamber 307 is at a relatively high pressure because of high formation fluid pressure. However, as noted above, it is desirable to maintain the gas chamber 311 at a relatively low pressure, such as atmospheric or subatmospheric pressure, to reduce collisional broadening of the molecular spectra. In one aspect, the pressure in chamber 311 is maintained in the range of 6% to 10% of the atmospheric pressure. Any other pressure also may be used. Collisional broadening widens the otherwise narrow optical absorption bands of gaseous molecules and, in some cases, can make them overlap, which can limit the ability to detect subtle spectral differences such as the differences that may distinguish molecules comprised of different isotopes of the same atoms. To maintain the pressure at a desired low pressure in chamber 311, a suitable pump 320 coupled to the chamber 311 via a line 352. The extracted gas and vapors from chamber 311 may be exhausted into a chamber 350. Pressure sensor 355 associated with chamber 311 provides pressure measurements to the processor 315. To test another sample such as at a different location in the same well, the tool 50 is moved to such a location to extract fluid. The fluid extracted from the second location moves the fluid already present in chamber 307 to the wellbore via valve 332 and replenishes the chamber 307 with the new fluid. The pump 320 aids in removing gas or vapors diffused into the chamber 311 from the prior location. To analyze a sample from a different well, the chambers 307 and 311 may be flushed at the surface. In another aspect, the chamber 311 may be evacuated to a desired low pressure before deployment into the wellbore 104. Also, the formation fluid may be pumped by pumping system (not shown) into the well until the fluid is clear and then diverting the clean fluid into the chamber 307.

In the above methods, the measurement and analysis is done separately for each fluid sample. In another aspect, the invention provides for making measurements continuously. The low pressure chamber 311 is filled (to a desired level with a chemically-inactive (inert) gas, such as Argon. Then, the sample chamber 311 can be continuously regenerated by using a sorbent to remove chemically active gases and vapors such as hydrocarbon and water vapors from the formation fluids that diffuse into the chamber 311. Any suitable sorbents may be used for the purpose of the present system. For example, synthetic zeolites, such as molecular sieve 3A, may be used as a water sorbent. For heavier hydrocarbons, activated charcoal may be used. For lighter hydrocarbons, such as methane, ethane and propane, which are typically weakly bound by charcoal, methane storage sorbents, such as sorbents known as isoreticular metal organic frameworks (IR-MOFs) may be used. IRMOFs have $OZn_4$ as their basic construction units, an oxygen atom at the center of a tetrahedron of zinc atoms, and a zinc atom connected by various organic compounds. The partition coefficient for a light hydrocarbon gas remaining in Argon versus adsorbing on the sorbent will favor sorption of the hydrocarbon. To reduce or minimize residual light hydrocarbon gases in the Argon atmosphere, the sorbent bed may be cooled.

In another aspect, the present system may be used as a cumulative sensor. In this aspect, the concentration of the hydrocarbons and water vapors in the low pressure chambers 311 is allowed to rise continuously instead of being sorbed. Then the readings are based on how the changes in the measured response of the mircoacoustic sensor changed over time instead of being based directly on the response itself. The laser 202 and the associated electronics may be housed in a temperature controlled enclosure 321. In one aspect, the enclosure for the laser may be a Dewar flask, which may contain a phase change material and have a heat pump, such as a thermoelectric or thermo-tunneling cooler, at its mouth to remove heat. In another aspect, the enclosure 321 may be a heat jacket that can maintain the temperature at a selected value or within a selected range. The processor 315 reports the analytical results to the surface via the wire line or other means of downhole communication.

Figure 6:
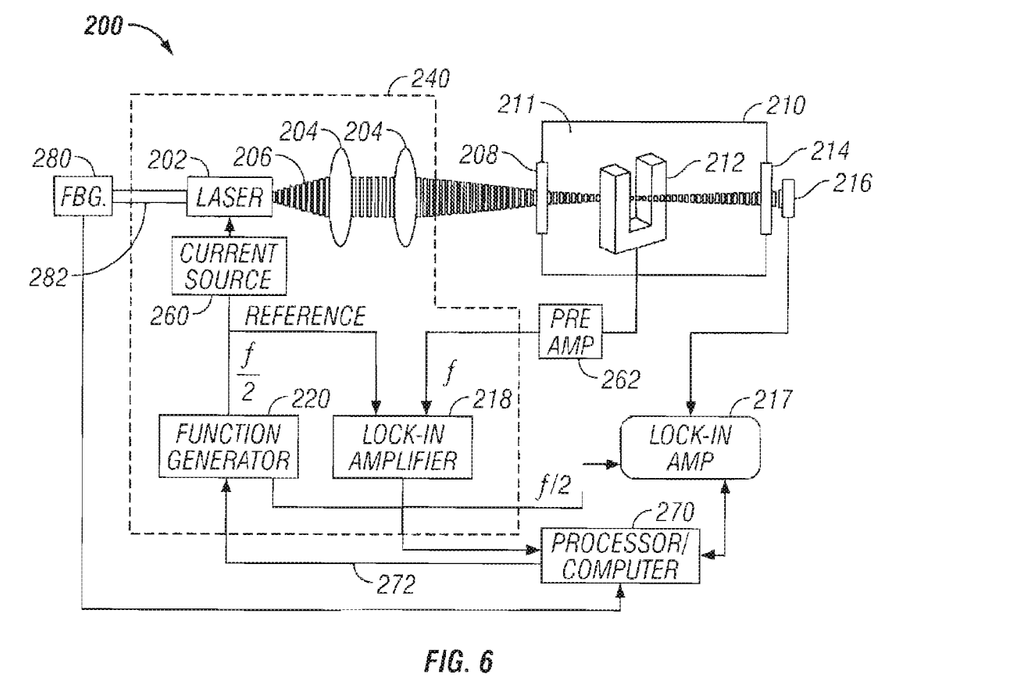
FIG. 6 is an illustration of a spectrometer based on Quartz Enhanced Photoacoustic Spectroscopy (QEPAS) for use in the present invention.

FIG. 6 is an illustration of a functional block diagram of the QEPAS system and method as provided by one aspect of the present invention. As shown in FIG. 6, a suitable arrangement for comprises a suitable tunable laser, which may be a distributed feedback (DFB) diode or interband cascade laser 202, that emits a laser beam 206 through collimation lenses 204. The laser beam 206 enters a window 208 and into a gas cell 210 which maybe in the form shown as chamber 311, FIG. 4. The dimensions and structures given herein are for example only and should not be construed as limiting to the scope of the invention. Gas cell 210 contains the gas mixture 211 under investigation, for example a mixture of water vapors and methane. To generate photoacoustic waves in the gases and vapors in cell 210, the laser 202 is tuned to a selected frequency. In one aspect, the laser is modulated at half the resonant frequency of the tuning fork 212. In one aspect, the tuning fork resonant frequency may be about 32 KHz and the laser frequency may be about 16 KHz. A commercially available tuning fork operates at 32768 Hz and has a Q factor of about 16,000. A suitable current to the laser is supplied by a current source 260. The response from the tuning fork 212 is amplified by a preamplifier 262 and passed to a lock-in amplifier 218. A function generator 220 supplies the reference frequency to both the lock-in amplifier 218 and the laser 202, which in the particular example noted-above, is half the resonant frequency (f) of tuning fork 212. The signals from the lock-in amplifier are processed by a processor or computer 270.

For the QEPAS technique, it is desirable to tune the laser to one or more narrow optical absorption wavelength of gaseous molecules. In one aspect, a photodetector may be used to tune the laser 202, wherein the laser beam 206 can be made to exit the cell 210 through window 214 disposed on the opposite of window 208. A photodector 216 detects the exiting laser beam 206. Signals from the photodetector 216 are processed by a lock-in amplifier 217 and passed to the computer 270 for processing. The computer 270 uses the results from the photodetector 216 to tune the laser via feedback 272. The function generator 220 also may supply the reference frequency to the lock-in amplifier 217. In another aspect, a Fiber Brag Grating (FBG) system may be used to tune the laser 202. In such a system, the laser beam may be split and a portion thereof 282 sent to a suitable FBG system 280. For example, one or more FBGs made out of ultra-low expansion glass may serve as one or more downhole wavelength standards or references and used for adjusting the wavelength of the laser 202 to match the desired molecular absorption wavelength. The laser wavelength may be adjusted by changing the current through the current source 260 or by changing the ambient temperature of the laser or by changing the spacing of the laser's Fabry Perot optical filter as is done in some commercial tunable diode lasers. The output from the FBG system 280 is processed by the computer 270 to control or alter the wavelength of the laser 202 via the feedback 272.

Figure 7:
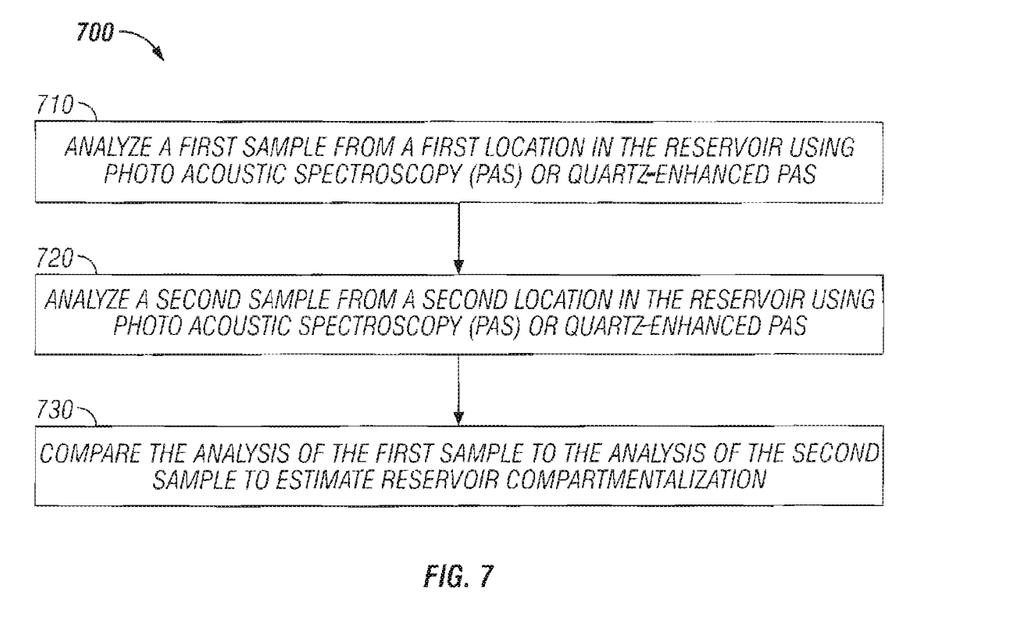
FIG. 7 is an illustration of a method performed according to one aspect of the present invention.

Turning now to FIG. 7, a flowchart 700 illustrating some of the functions performed by the present invention is illustrated. In block 710 the present invention analyzes a first sample taken from a first location in the reservoir. In block 720 the present invention analyzes a second sample taken from a second location in the reservoir. In block 730 the present invention estimates the degree of compartmentalization based on a comparison of the analysis for the samples taken from various locations in the reservoir.

The semi-permeable membrane between the fluid and the evacuated chamber allows gases from the fluid to diffuse through the semi-permeable membrane into an evacuated gas analysis chamber. The system of the present invention monitors the gases to detect, identify and quantify the gases and distinguish between them. A sorbent or an ion pump optionally removes diffused gases from the evacuated side of the chamber to maintain the vacuum. Ion pumps preferentially pump chemically active gases much better than inert gases. One can select an ion pump whose inert gas pumping is particularly slow so as to selectively remove formation gases and vapors from the inert gas that may be used to fill the low pressure chamber. Suitable commercially available semi-permeable membranes, residual gas analyzers and vacuum pumps may be used in the system of the present invention. Furthermore, membranes can be specially designed to be selective to the transmission of one gas instead of transmitting many gases as do most silicone membranes.

The analysis can be, but is not limited to, estimation of isotopic ratios, phytane/pristine ratios or any analytical comparison which yields a distinction between samples from a plurality of wells or a plurality of depths in the same well which is indicative of compartmentalization.

While the foregoing disclosure is directed to the exemplary embodiments of the invention, various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated. There are, of course, additional features of the invention that will be described hereinafter and which will form the subject of the claims appended hereto.

What is claimed is:

1. A method for estimating a selected characteristic of a formation fluid, comprising:
obtaining a first fluid sample that includes gas from a first location downhole;
separating at least a portion of the gas from the first fluid sample in a chamber downhole;
supplying laser energy to the gas separated from the first fluid sample to generate photoacoustic waves;
detecting the photoacoustic waves; and
estimating the selected characteristic of the first fluid sample utilizing the detected photoacoustic waves.

2. The method of claim 1, further comprising:
obtaining a second fluid sample from a second location downhole;
estimating whether the second fluid sample includes the selected characteristic; and
estimating a property of a reservoir from the estimated characteristic of the first fluid sample and the estimated characteristic of the second fluid sample.

3. The method of claim 2, wherein estimating the property of the reservoir comprises comparing the estimated characteristic of the first fluid sample and the estimated characteristic of the second fluid sample.

4. The method of claim 2, wherein estimating the characteristic of the first fluid sample and second fluid sample comprises estimating an isotopic ratio.

5. The method of claim 2, wherein estimating the characteristic of the first fluid sample and the second fluid sample comprises estimating a sample composition.

6. The method of claim 2, wherein estimating the property of the reservoir comprises comparing phytane and pristine ratios relating to the first and second fluid samples.

7. The method of claim 1, wherein detecting the photoacoustic waves comprises using a photoacoustic spectrometer or a quartz-enhanced photoacoustic spectrometer.

8. The method of claim 1, wherein separating gas from the first fluid sample comprises diffusing gas from the first fluid sample into the chamber that is at least partially evacuated.

9. An apparatus for use downhole, comprising:
a probe configured to retrieve a formation fluid;
a chamber configured to receive gas from the retrieved formation fluid;
an energy source configured to induce energy into the gas to generate photoacoustic waves;
a photoacoustic spectrometer configured to estimate a characteristic of the gas from the photoacoustic waves; and
a processor configured to estimate a property of a reservoir utilizing the estimated characteristic of the gas.

10. The apparatus of claim 9, wherein the photoacoustic spectrometer is a quartz-enhanced photoacoustic spectrometer.

11. The apparatus of claim 9, wherein the property of the reservoir is compartmentalization and wherein the processor is configured to estimate compartmentalization by comparing the characteristic of gas separated from formation fluids maintained at two separate downhole locations.

12. The apparatus of claim 11, wherein the processor is further configured to estimate the reservoir compartmentalization by using an isotopic ratio.

13. The apparatus of claim 9, wherein the energy source is a laser carried by the apparatus and wherein the apparatus further comprises a tuning fork resonator in the chamber configured to detect the photoacoustic waves.

14. The apparatus of claim 9, wherein the processor is located at one of: (i) in a portion of the apparatus that is configured to be deployed in a wellbore; and (ii) at a surface location.

15. The apparatus of claim 9, wherein the processor is further configured to compare phytane and pristine ratios to estimate the property of the reservoir.

16. The apparatus of claim 9, wherein the processor is further configured to estimate composition of the fluid to estimate the property of the reservoir.

17. The apparatus of claim 9, wherein the processor is further configured to estimate a distinguishing characteristic of the fluid.

* * * * *